(12) United States Patent
Nadkarni et al.

(10) Patent No.: US 11,413,239 B2
(45) Date of Patent: *Aug. 16, 2022

(54) PHARMACEUTICAL COMPOSITION OF TAPENTADOL FOR NASAL ADMINISTRATION

(75) Inventors: Sunil Sadanand Nadkarni, Gujarat (IN); Jaya Abraham, Gujarat (IN); Kapil Khatri, Gujarat (IN); Vipul Mittal, Gujarat (IN)

(73) Assignee: Torrent Pharmaceuticals Ltd., Gujarat (IN)

( * ) Notice: Subject to any disclaimer, the term of this patent is extended or adjusted under 35 U.S.C. 154(b) by 786 days.

This patent is subject to a terminal disclaimer.

(21) Appl. No.: 14/233,265

(22) PCT Filed: Jul. 19, 2012

(86) PCT No.: PCT/IB2012/053683
§ 371 (c)(1),
(2), (4) Date: Jan. 16, 2014

(87) PCT Pub. No.: WO2013/011477
PCT Pub. Date: Jan. 24, 2013

(65) Prior Publication Data
US 2014/0170209 A1    Jun. 19, 2014

(30) Foreign Application Priority Data
Jul. 20, 2011    (IN) .......................... 2063/MUM/2011

(51) Int. Cl.
| | |
|---|---|
| *A61K 31/137* | (2006.01) |
| *A61K 9/08* | (2006.01) |
| *A61K 9/00* | (2006.01) |
| *A61K 47/10* | (2017.01) |
| *A61K 47/18* | (2017.01) |

(52) U.S. Cl.
CPC .............. *A61K 9/0043* (2013.01); *A61K 9/08* (2013.01); *A61K 31/137* (2013.01); *A61K 47/10* (2013.01); *A61K 47/18* (2013.01)

(58) Field of Classification Search
CPC ...... A61K 9/0043; A61K 9/08; A61K 31/137; A61K 47/10; A61K 47/18
USPC ....................................................... 424/400
See application file for complete search history.

(56) References Cited

U.S. PATENT DOCUMENTS

| | | | |
|---|---|---|---|
| 5,629,011 A | 5/1997 | Illum | |
| 6,248,737 B1 | 6/2001 | Buschmann et al. | |
| 2005/0142072 A1* | 6/2005 | Birch .................. | A61K 9/0043 424/46 |
| 2006/0110333 A1 | 5/2006 | Yanagawa | |
| 2010/0063148 A1 | 3/2010 | Christoph et al. | |
| 2010/0227921 A1 | 9/2010 | Franklin et al. | |

FOREIGN PATENT DOCUMENTS

| | | |
|---|---|---|
| WO | WO 2005/020906 | 3/2005 |
| WO | WO 2012/119727 | 9/2012 |

OTHER PUBLICATIONS

Dale et al., "Nasal administration of opioids for pain management in adults", Acta Anaesthesiol Scand, vol. 46, 2002, pp. 759-770.
International Search Report and Written Opinion from International Application No. PCT/IB2012/053683 dated Nov. 16, 2012.
Somogyi et al., "Pharmacogenetics of Opioids", Clinical Pharmacology & Therapeutics, vol. 81, No. 3, 2007, pp. 429-444.
Terlinden et al., "Absorption, metabolism, and excretion of $^{14}$C-labeled Tapentadol HCI in healthy male subjects", European Journal of Drug Metabolism and Pharmacokinetics, vol. 32, No. 3, 2007, pp. 163-169.
Tapentadol: Clinical Study Report Synopsis R331333-PAI-3003 (KF5503/32), pp. 1-6.
Terlinden et al., Pharmacokinetics, excretion, and metabolism of tapentadol HCI, a novel centrally acting analgesic, in healthy subjects, J. Pain (2006) 7(suppl 1), S26, Abst. No. 689.
Pathak, Vinayak, "Nasal Delivery—A Promising Route of Drug Delivery to the Brain: Scientific Considerations" 1-13; Mar. 2018 https://drug-dev.com/nasal-delivery-a-promising-route-of-drug-delivery-to-the-brain-scientifc-considerations-2/.
KuKanish, B. and Philip Allen, "Comparative pharmacokinetics of intravenous fentanyl and buprenorphine in healthy Greyhound dogs", J Vet Pharmacol Ther., 1-6, 2014 PMID: 24684621 https://www.ncbi.nlm.nih.gov/pmc/articles/PMC4219927/#:~:text=Buprenorphine is a lipophilic mu, %2C et al%2C 1994).
Upadhyay, S., et al., "Intranasal drug delivery system—A glimpse to become maestro", Journal of Applied Pharmaceuticals Science 01 (03); 34-44 (2011) www.japsonline.com.
Beckett, A.H. and R.D. Hossie, "Buccal Absorption of Drugs", Chapter 3 Concepts in Biochemical Pharmacology, B.B. Brodie et al. editors, Springber-Verlag Berlin, Heidelberg, 1971 pp. 25-26.
Dale, O., et al., "Nasal administration of opioids for pain management in adults", ACTA Anaesthesiol Scand, 46:759-770 (2002).

* cited by examiner

*Primary Examiner* — Adam C Milligan

(74) *Attorney, Agent, or Firm* — Melissa M. Hayworth; E. Joseph Gess

(57) ABSTRACT

The present invention relates to a pharmaceutical composition of tapentadol for nasal administration. Present invention also relates to the process of preparation of pharmaceutical composition of tapentadol for nasal administration and its use in the treatment of pain.

8 Claims, 1 Drawing Sheet

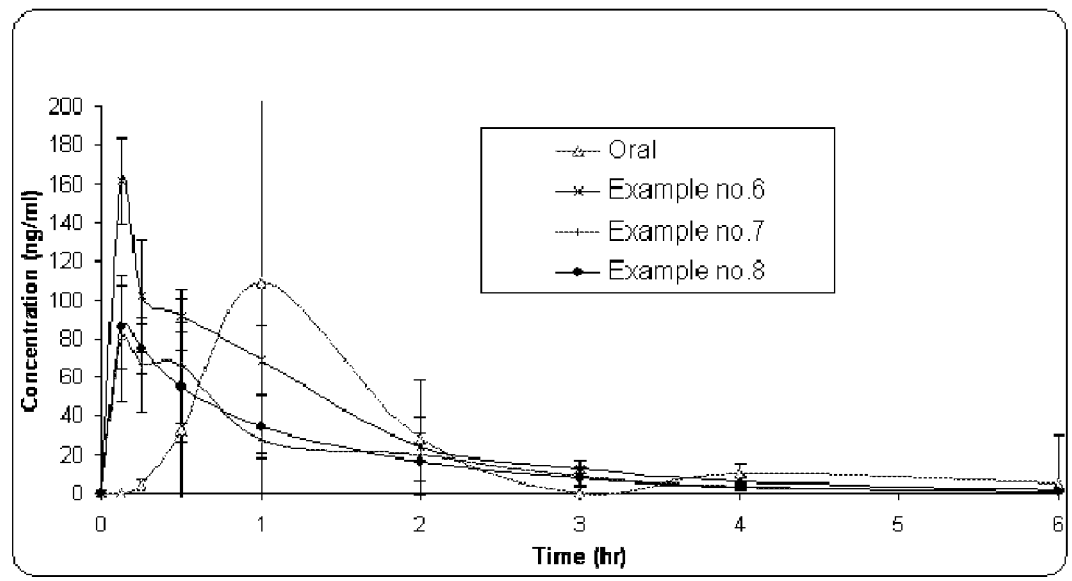

PHARMACEUTICAL COMPOSITION OF TAPENTADOL FOR NASAL ADMINISTRATION

This application is a National Stage Application of PCT/IB2012/053683, filed 19 Jul. 2012, which claims benefit of Serial No. 2063/MUM/2011, filed 20 Jul. 2011 in India and which applications are incorporated herein by reference. To the extent appropriate, a claim of priority is made to each of the above disclosed applications.

FIELD OF THE INVENTION

The present invention relates to pharmaceutical compositions for nasal administration, their preparation and their use in the treatment of pain. In particular, the present invention relates to a pharmaceutical composition of tapentadol for nasal administration for the management of pain.

BACKGROUND OF THE INVENTION

Tapentadol is 3-[(1R,2R)-3-(dimethylamino)-1-ethyl-2-methylpropyl]phenol. A particularly preferred form is the hydrochloride salt, 3-[(1R,2R)-3-(dimethylamino)-1-ethyl-2-methylpropyl]phenol monohydrochloride. Tapentadol is highly soluble drug and its solubility is pH dependent. It is considered as BCS class-I drug.

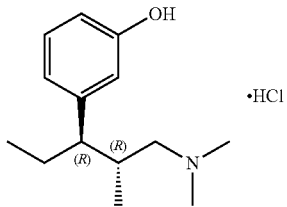

Tapentadol is a centrally acting analgesic having both μ-opioid receptor agonist and noradrenalin (Norepinephrine) reuptake inhibition activity with minimal serotonin reuptake inhibition. This dual mode of action makes tapentadol particularly useful in the treatment of both nociceptive pain and neuropathic pain. Clinical trial evidence in acute and chronic non-cancer pain, cancer related pain and neuropathic pain supports an opioid-sparing effect that reduces some of the typical opioid-related adverse effects. Specifically, the reduction in treatment-emergent gastrointestinal adverse effects for tapentadol compared with equi-analgesic pure μ-opioid receptor agonist results in improved tolerability and adherence to therapy.

U.S. Pat. No. 6,248,737 discloses tapentadol and its hydrochloride salt. Tapentadol is available commercially as a brand name NUCYNTA® as 50 mg, 75 mg and 100 mg oral tablet, indicated for the relief of moderate to severe acute pain.

When tapentadol is given orally, it undergoes extensive first pass metabolism, which leads to achieve low bioavailability (32%). About 97% of the parent compound is metabolized. None of the metabolites contributes to the analgesic activity. Lipid solubility of tapentadol is approximately 2.8, which is comparatively low. Being an opioid analgesic, tapentadol is useful for the treatment of severe pain such as post operative pain, cancer pain etc. In such cases nausea and vomiting is a frequently associated problem and hence poor patient compliance is seen with oral administration. Moreover, for the treatment of breakthrough pain oral formulations are inadequate as it needs at least 45 minutes to absorb after administration, which is not suitable in the treatment of breakthrough pain, as this delay in absorption is typically longer than the episode of breakthrough pain. The maximum serum concentration of tapentadol is typically observed at around 1.25 hours after oral dosing. The bitter taste of tapentadol is not patient friendly, which eventually leads to non adherence to the drug therapy.

Generally, opioids are known to show higher inter-subject variability (*Clinical pharmacology and therapeutics;* 2007; 81; 429-444). Exact reasons for such variability are not yet characterized completely but genetic polymorphism of opioid receptors, species effect, metabolic effect or placebo related phenomenon can be possible reasons. It has been observed that the route of administration also have great impact on inter-subject variability. It has been observed that variation of absorption after intranasal route may be a greater than intramuscular or sc route (*Acta Anaesthesiol Scand* 2002; 46; 759-770). Like other opioids, tapentadol also has high inter-subject variability, when given orally, as given in *Tapentadol clinical study report synopsis R331333-PAI*-30003 (KF 5503/32). High clearance of the tapentadol may be one of the reasons of this high inter-subject variability.

Thus, there exists need for an alternative dosage form of tapentadol which overcomes the above problems such as bitter taste, adverse effects etc and moreover provides quick onset of action with reduction of inter-subject variability and improved patient compliance.

WO2005020906 discloses intranasal opioid composition for pain management with improved bioavailability and improved patient compliance.

US2006110333 discloses a composition for nasal absorption of opioid comprises calcium carbonate and/or calcium phosphate having particle size of up to 500 μm, with lower risk of developing side effects as compared to oral route.

U.S. Pat. No. 5,629,011 discloses a composition for nasal administration comprises polar metabolite of opioid analgesic consists of glucoronides and ethereal sulphates of opioid analgesics.

US201000227921 discloses that tapentadol is associated with high inter-patient variability and therefore a uniform patient response may be lacking. Therefore, to overcome the problems, amino acids and peptide carbamate pro-drugs of tapentadol are prepared.

The prior art does not provide a suitable dosage form of tapentadol which masks the bitter taste thereby being more palatable to patients whilst at the same time providing a quick onset of action.

Inventors of present inventions have discovered intranasal formulation of tapentadol, which surprisingly overcome many problems associated with oral formulation, which provides comparative bioavailability to oral formulation and also reduces intersubject variability.

OBJECTS OF THE INVENTION

It is an object of the present invention to overcome the drawbacks of the prior arts.

It is another object of the present invention to provide a nasal composition comprising tapentadol or its pharmaceutically acceptable salt(s) and at least one nasal carrier.

It is yet another object of the present invention to provide a pharmaceutical product comprising a nasal composition and a dispensing device wherein the device is adapted for administering the composition to the nasal mucosa.

It is another object of the present invention to provide a process for the preparation of a composition comprising the step of mixing tapentadol or its pharmaceutically acceptable salt(s) with at least one nasal carrier.

SUMMARY OF THE INVENTION

The present invention relates to a nasal composition comprising tapentadol or its pharmaceutically acceptable salt(s) and at least one nasal carrier.

It is another aspect of the present invention to provide a nasal composition comprising tapentadol or its pharmaceutically acceptable salt and at least one nasal carrier, in combination with instructions for use by nasal administration.

It is another aspect of the present invention to provide a nasal composition comprising tapentadol or its pharmaceutically acceptable salt(s) wherein inter-subject variability in Tmax is less than 50%, preferably less than 40%, more preferably less than 30%, most preferably less than 20%, when administered to mammal.

It is another aspect of the present invention to provide a nasal composition comprising tapentadol or its pharmaceutically acceptable salt(s) wherein inter-subject variability in Cmax is less than 50%, preferably less than 40%, more preferably less than 30%, most preferably less than 20%, when administered to mammal.

It is another aspect of the present invention to provide a nasal composition comprising tapentadol or its pharmaceutically acceptable salt(s) wherein inter-subject variability in AUC is less than 50%, preferably less than 40%, more preferably less than 30%, most preferably less than 25%, when administered to mammal.

It is another aspect of the present invention to provide a nasal composition comprises tapentadol or its pharmaceutically acceptable salt(s) formulated as liquid, wherein Tmax is characterized as having inter-subject variability of less than 50%, preferably less than 40%, more preferably less than 30%, most preferably less than 20%, when administered to mammal.

It is another aspect of the present invention to provide a nasal composition comprises tapentadol or its pharmaceutically acceptable salt(s) formulated as liquid, wherein Cmax is characterized as having inter-subject variability of less than 50%, preferably less than 40%, more preferably less than 30%, most preferably less than 20%, when administered to mammal.

It is another aspect of the present invention to provide a nasal composition comprises tapentadol or its pharmaceutically acceptable salt(s) formulated as liquid, wherein AUC is characterized as having inter-subject variability of less than 50%, preferably less than 40%, more preferably less than 30%, most preferably less than 25%, when administered to mammal.

It is another aspect of the present invention to provide a nasal composition comprising tapentadol or its pharmaceutically acceptable salt and at least one nasal carrier wherein Cmax is achieved in less than 45 minutes when administered to mammal.

It is another aspect of the present invention to provide a nasal composition comprising tapentadol or its pharmaceutically acceptable salt and at least one nasal carrier, wherein the pH of the nasal composition is from 3.0 to 9.0, preferably from 3.0 to 8.0, more preferably from 3.0-7.0 and most preferably from 4.0-6.0.

It is another aspect of the present invention to provide a nasal composition comprising tapentadol or its pharmaceu-tically acceptable salt and at least one nasal carrier wherein a unit dose of the composition has a volume of from 25 µl to 150 µl, preferably 100 µl to 130 µl.

It is yet another aspect of the present invention to provide a pharmaceutical product comprising a nasal composition and a dispensing device wherein the device is adapted for administering the composition to the nasal mucosa.

It is another aspect of the present invention to provide a process for the preparation of a composition comprising the step of mixing tapentadol or its pharmaceutically acceptable salt(s) with at least one nasal carrier.

FIG. 1: Comparative pharmacokinetic profile of nasal formulations vs oral formulation in rabbits

DETAILED DESCRIPTION OF THE INVENTION

The following paragraphs detail various embodiments of the invention. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent important aspects of the invention that may be taken in isolation and combined with other important aspects of the invention described elsewhere within this specification as a whole, and including the examples and FIGURE. The skilled person will appreciate that the invention extends to such combinations of features and that these have not been recited in detail here in the interests of brevity.

The term "tapentadol" as used herein is defined to mean at least one form of tapentadol chosen from tapentadol base, the individually optically active enantiomers of tapentadol, racemic mixtures thereof, active metabolites thereof, pharmaceutically acceptable salts thereof or polymorph thereof. Any of these said forms can be crystalline or amorphous.

The pharmaceutically acceptable salts of tapentadol according to the invention are acid addition salts wherein acid is selected from hydrochloric acid, hydrobromic acid, embonic acid, (2S.3S)-dibenzoyltartaric acid, dibenzoyltartaric acid, sebacic acid, 1-hydroxys-naphthoic acid, phosphoric acid, L-(+)-tartaric acid, lysinic acid, L-lysinic acid, D-(+)-malic acid, 4-methylbenzenesulfonic acid, ethanesulfonic acid, benzoic acid, cinnamic acid, L-(+)-lactic acid, S-(+)-mandelic acid, (+)-camphor-10-sulfonic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, nicotinic acid, hydrogen bromide, sulfuric acid, acetic acid, propionic acid, oxalic acid, succinic acid, fumaric acid, maleic acid, hippuric acid, lactic acid, mandelic acid, malonic acid, malic acid, tartaric acid, methanesulfonic acid, citric acid, lactic acid. Preferably hydrochloric acid addition salt of tapentadol is used for the present invention and any embodiment thereof.

The term "liquid composition" as used herein is defined as a solution, suspension or dispersion.

The term "Crystal growth inhibitor" as used herein is defined as an agent which facilitates in formation of homogenous nasal composition of tapentadol.

The term "inter-subject variability" as used herein is defined as the variability in response which occurs between subjects in an experiment or in patient population or in a group of people, administered with a drug or a composition. The inter subject variability is represented in the form of coefficient of variation.

The term "Mammal" as used herein is defined as a human or an animal such as monkeys, primates, dogs, cats, horses, cows, rabbit and the like.

The use of the terms "a" and "an" and "the" and similar references in the context of describing the invention (especially in the context of the following claims) are to be construed to cover both the singular and the plural, unless otherwise indicated herein or clearly contradicted by context.

It is well known to the skilled person that apart from many factors, lipid solubility play crucial role in the absorption of drug through nasal mucosa. Drugs with high lipophilicity have higher tendency to get absorbed through nasal mucosa compared to almost negligible absorption of low lipophilicity drugs. It has been tested that, intranasal formulations of low lipophilicity drugs like morphine gives less bioavailability as compared to intravenous administration, when given in solution form. Therefore they are required to be given with agent like chitosan which provides longer time for drug transport across the nasal membrane, before the formulation is cleared by the mucociliary clearance mechanism.

Surprisingly, it has been found that nasal composition of tapentadol can be prepared according to present invention having good absorption and comparative bioavailability to oral composition in spite of its low lipid solubility.

The nasal composition of tapentadol of the present invention provides a quick onset of action as compared to the oral route. The $C_{max}$ can be achieved in a shorter period of time as compared to the oral route.

Tapentadol is a high clearance drug (Cl=1468.+−.122 mL/min) and consequently exhibits low oral bioavailability (Eur. J. Drug Met and Pharmacokinetics; 2007; 32; 163-169). This high clearance results in wide inter-patient variability in plasma drug concentrations (relative standard deviation in Cmax is 46%) Surprisingly, inter-subject variability is found lower with intranasal formulation of tapentadol compared to oral formulation.

Therapeutic administration of tapentadol requires a high drug dose for nasal administration. It is difficult to formulate a nasal composition of tapentadol as each single dose must have a volume limitation (maximum volume limitation is 150 µl/nostril) so that the target dose delivery can be achieved without causing irritation. Volume limitation is an important factor when considering nasal administration; if the volume exceeds the maximum volume limitation, the formulation will drain from the pharynx or may run out from the nostrils; conversely, if the formulation is significantly less than the maximum volume limitation, a high concentration of tapentadol will be required to achieve the target dose, which eventually leads to high osmolality and causes irritation to the nasal cavity. Present invention provides a nasal composition wherein a unit dose of the composition has a volume of from 25 µl to 150 µl, preferably 100 µl to 130 µl.

It is observed that increase in concentration of the tapentadol in the solution leads to formation of crystals, when stored for extended duration (for more than 3 days). This makes the formulation non-homogeneous and therefore non-suitable for nasal administration. This crystal growth may further leads to altered therapeutic effect of the drug. Present invention overcomes this problem by providing a composition, wherein no such crystal growth is observed in the composition comprising high concentration of drug, when stored for longer duration.

The present invention is to provide a nasal composition comprising tapentadol or its pharmaceutically acceptable salt(s) and at least one nasal carrier.

The present invention is to provide a nasal composition comprising tapentadol hydrochloride and at least one nasal carrier.

A nasal carrier according to present invention may be selected from the group consisting of buffering agent, isotonicity agent, preservative, permeation enhancer, stabilizer, solubilizer, chelating agent, antioxidant, mucoadhesive agent, viscosity modifying agent, humectants, sweetener, taste masking agent, solvents, co-solvents, in-situ gelling agent, surfactant, polymer, thickening agent, lubricant, bulking agent, colorant, oil, phospholipids and flavoring agent.

Another embodiment of the present invention provides a nasal composition comprising tapentadol or its pharmaceutically acceptable salt(s) and at least one nasal carrier, wherein the composition is formulated as a liquid composition.

Another embodiment of the present invention provides a nasal composition comprising tapentadol hydrochloride and at least one nasal carrier, wherein the composition is formulated as a liquid composition.

Another embodiment of the present invention provides a nasal composition comprising tapentadol or its pharmaceutically acceptable salt(s) and at least one nasal carrier, wherein the composition is formulated as a liquid composition, and wherein the liquid composition is in the form of aqueous solution.

Another embodiment of the present invention provides a nasal composition comprising tapentadol hydrochloride and at least one nasal carrier, wherein the composition is formulated as a liquid composition, and wherein the liquid composition is in the form of aqueous solution.

Another embodiment of the present invention provides a nasal composition comprising tapentadol or its pharmaceutically acceptable salt(s) and at least one nasal carrier selected from the group consisting of buffering agent, isotonicity agent, preservative, permeation enhancer, stabilizer, chelating agent, antioxidant, mucoadhesive agent, viscosity modifying agent, humectants, sweetener, taste masking agent, solvents, co-solvents, thickening agent, solubilizer, flavoring agent, and surfactant, wherein the composition is formulated as a liquid composition.

Another embodiment of the present invention provides a nasal composition comprising tapentadol or its pharmaceutically acceptable salt(s) and at least one nasal carrier formulated as a liquid composition, and wherein the said composition forms a gel in-situ after nasal administration.

Another embodiment the of present invention provides a nasal composition comprising tapentadol or its pharmaceutically acceptable salt(s) and at least one nasal carrier selected from the group consisting of in-situ gelling agent, mucoadhesive agent, polymer, humectant, buffering agent, stabilizer, surfactant, preservative, thickening agent, solvents, co-solvents, permeation enhancer, chelating agent, viscosity modifying agent, sweetener, taste masking agent, solubilizer, flavoring agent, and isotonicity agent formulated as a liquid composition, and wherein the said composition forms gel in-situ after nasal administration.

Another embodiment of the present invention provides a nasal composition comprises tapentadol or its pharmaceutically acceptable salt(s) and at least one nasal carrier, wherein the composition is formulated as a gel composition.

Another embodiment of the present invention provides a nasal composition comprising tapentadol or its pharmaceutically acceptable salt(s), polymer and at least one nasal carrier selected from the group consisting of mucoadhesive agent, viscosity modifying agent, humectant, chelating agent, buffering agent, solvents, co-solvents, permeation enhancer, sweetener, taste-masking agent, solubilizer, flavoring agent, surfactant, preservative and stabilizer, wherein the composition is formulated as gel composition.

Another embodiment of the present invention provides a nasal composition comprising tapentadol or its pharmaceutically acceptable salt(s) and at least one nasal carrier, wherein the composition is formulated as powder composition.

Another embodiment of the present invention provides a nasal composition comprising tapentadol or its pharmaceutically acceptable salt(s) and at least one nasal carrier selected from the group consisting of mucoadhesive agent, lubricant, preservative, permeation enhancer, sweetener, taste-masking agent, flavoring agent, bulking agent and colorant, wherein the composition is formulated as powder composition.

Another embodiment of the present invention provides a nasal composition comprising tapentadol or its pharmaceutically acceptable salt(s) and at least one nasal carrier, wherein the composition is formulated as micro/nanoemulsion composition.

Another embodiment of the present invention provides a nasal composition comprising tapentadol or its pharmaceutically acceptable salt(s), oil and at least one nasal carrier selected from the group consisting of polar solvent, co-solvent, surfactant, mucoadhesive agent, buffering agent, isotonicity agent, permeation enhancer, chelating agent, viscosity modifying agent, taste masking agent, solubilizer, preservative, flavoring agent, stabilizer and sweetener, wherein the composition is formulated as micro/nanoemulsion composition.

Another embodiment of the present invention provides a nasal composition comprising tapentadol or its pharmaceutically acceptable salt(s) and at least one nasal carrier, wherein the composition is formulated as a liposome composition.

Another embodiment of the present invention provides a nasal composition comprising tapentadol or its pharmaceutically acceptable salt(s), phospholipids and optionally at least one nasal carrier selected from the group consisting of antioxidant, chelating agent, buffering agent, preservative, mucoadhesive agent, taste-masking agent, viscosity modifying agent, isotonicity agent, flavoring agent and sweetener, wherein the composition is formulated as a liposome composition.

The present invention is to provide a nasal composition comprising tapentadol or its pharmaceutically acceptable salt(s) and at least one nasal carrier, and wherein the pH of the nasal composition is from 3.0 to 9.0, preferably from 3.0 to 8.0, more preferably from 3.0-7.0 and most preferably from 4.0-6.0.

Another embodiment of the present invention provides a nasal composition comprising tapentadol hydrochloride and at least one nasal carrier formulated as a liquid composition, and wherein the pH of the said composition is from 3.0 to 9.0, preferably from 3.0 to 8.0, more preferably from 3.0-7.0 and most preferably from 4.0-6.0.

Another embodiment of present invention provides a nasal composition comprising tapentadol or its pharmaceutically acceptable salt(s) and at least one crystal growth inhibitor.

Another embodiment of present invention provides a nasal composition comprising tapentadol or its pharmaceutically acceptable salt(s) and at least one viscosity modifying agent wherein the viscosity of the said formulation is equal to or less than 100 cps, preferably equal to or less than 50 cps, most preferably equal to or less than 30 cps.

Another embodiment of the present invention provides a nasal composition comprising tapentadol or its pharmaceutically acceptable salt(s) and a preservative. Preferably the preservative is benzalkonium chloride. The invention also provides a nasal composition comprising tapentadol or its pharmaceutically acceptable salt(s), benzalkonium chloride and sodium chloride.

Another embodiment of the present invention provides a nasal composition comprising tapentadol or its pharmaceutically acceptable salt(s), a preservative, at least one nasal carrier and a sweetener. Preferably, the preservative is benzalkonium chloride. Preferably, the sweetener is sucralose or neotame. Preferably, nasal carrier is hydroxypropylmethyl cellulose or sodium carboxymethylcellulose or mixture thereof. The invention also provides a nasal composition comprising tapentadol hydrochloride, benzalkonium chloride, sodium chloride and sucralose or neotame. The composition may further comprise a humectant (for example sorbitol), and/or a further nasal carrier selected from a polymer, a mucoadhesive agent and a viscosity modifying agent. The composition may further comprise a surfactant such as polyoxyethylene-polyoxypropylene copolymer. The invention further provides a nasal composition comprising tapentadol or its pharmaceutically acceptable salt(s), sorbitolhydroxy propylmethyl cellulose, sucralose, polyoxyethylene-polyoxypropylene copolymer and benzalkonium chloride.

Another embodiment of the present invention provides a nasal composition comprising tapentadol or its pharmaceutically acceptable salt(s), a preservative and a humectant. Preferably, the preservative is benzalkonium chloride. Preferably the humectant is sorbitol or polyethylene glycol. The composition may comprise a further nasal carrier selected from an in-situ gelling agent, a thickening agent and a mucoadhesive agent, such as genu pectin and/or sodium alginate. The invention also provides a nasal composition comprising tapentadol or its pharmaceutically acceptable salt(s), genu pectin, sodium alginate, sorbitol and benzalkonium chloride.

Another embodiment of the present invention provides a nasal composition comprising tapentadol or its pharmaceutically acceptable salt(s), a preservative, a humectant and a solvent. The composition may also comprise a sweetener, such as sucralose or neotame. Preferably, the preservative is benzalkonium chloride. Preferably the humectant is sorbitol or polyethylene glycol. Preferably, the solvent is propylene glycol. The composition may comprise a further nasal carrier selected from an anti-oxidant and a stabiliser, such as butylate hydroxyl toluene. The invention also provides a nasal composition comprising tapentadol or its pharmaceutically acceptable salt(s), polyethylene glycol, propylene glycol, butylate hydroxyl toluene and sucralose.

Another embodiment of the present invention provides a nasal composition comprising tapentadol or its pharmaceutically acceptable salt(s), at least one nasal carrier and a crystal growth inhibitor. Preferably, the crystal growth inhibitor is polyoxyethylene-polyoxypropylene copolymer. Preferably, nasal carrier is hydroxypropylmethyl cellulose or sodium carboxymethylcellulose or mixture thereof.

The nasal composition comprising tapentadol, or its pharmaceutically acceptable salt(s), according to present invention, provides comparative bioavailability as oral composition of tapentadol. Being a drug with low lipophilicity, tapentadol is expected to have poor absorption across the mucous membrane and hence low bioavailability. Surprisingly, it has been found that a nasal composition according to present invention provides bioavailability equivalent to its oral composition.

The invention also provides a pharmaceutical product comprising a nasal composition as described herein and a dispensing device wherein the device is adapted for administering the composition to the nasal mucosa. For example, the device may comprise a nasal pump so that the product is in the form of a nasal spray. Alternatively the device may comprise another suitable nasal applicator. The pharmaceutical product may further comprise instruction for use, for example in the form of an insert or label.

Another embodiment of the present invention provides a nasal composition comprising tapentadol or its pharmaceutically acceptable salt(s) for the treatment of pain and in particular acute pain. The nasal composition is according to any one of the compositions described herein.

Also provided does the use of a nasal composition comprise tapentadol or its pharmaceutically acceptable salt(s) in the treatment of acute pain. The nasal composition is according to any one of the compositions described herein.

Further provided is a method of treating pain, and particularly acute pain, comprising administering to a subject in need thereof, a nasal composition comprising tapentadol or its pharmaceutically acceptable salt(s). The nasal composition is according to any one of the compositions described herein.

The acute pain according to present invention is selected from but not limited to breakthrough cancer pain, dental pain or pain associated with the medical conditions which include day care surgeries, appendicectomy, cholecystectomy, nailing, plating, fixation of fractured bone, burns dressing, jejunostomy dressing and wound dressing.

Another embodiment of the present invention provides a process for the preparation of a nasal composition comprising tapentadol or its pharmaceutically acceptable salt(s) and at least one nasal carrier. The process comprises the step of mixing tapentadol or its pharmaceutically acceptable salt(s) with at least one nasal carrier.

In another embodiment, the present invention provides a nasal composition comprising 1 to 50% w/w of tapentadol or its pharmaceutically acceptable sat(s), Preferably 5 to 50% of tapentadol or its pharmaceutically acceptable sat(s), more preferably 5 to 40% of tapentadol or its pharmaceutically acceptable sat(s), most preferably 5 to 30% of tapentadol or its pharmaceutically acceptable salt(s).

In another embodiment, the present invention provides a nasal composition comprising tapentadol, wherein the said composition achieves the Cmax in a period ranging from 5 to 45 minutes, preferably from 7 to 30 minutes, more preferably from 7 to 20 minutes when administered to mammal.

The nasal composition according to present invention provides less inter-subject variability as compared to oral formulation, when administered to mammal. The inter-subject variability in Tmax, AUC and Cmax is preferably less than about 50%, preferably less than 40%, more preferably less than 30%, most preferably less than 25%. The inter-subject variability in Tmax and Cmax is preferably lower than 20%.

Liquid Composition

Nasal composition of the present invention can be formulated as a liquid composition which can be of aqueous or non aqueous solution, preferably aqueous solution. The pH of the nasal liquid composition is within a range of 3.0 to 9.0, preferably from 3.0 to 8.0, more preferably from 3.0 to 7.0 and most preferably from 4.0-6.0. The nasal composition also comprises at least one nasal carrier.

Nasal carrier used in the liquid composition is selected from buffering agent, isotonicity agent, preservative, permeation enhancer, stabilizer, solubilizer, chelating agent, antioxidant, mucoadhesive agent, viscosity modifying agents, humectants, sweeteners, taste masking agents, solvents, co-solvents, thickening agent, flavoring agent, or surfactant. The said composition of the present invention also includes diluents. Suitable diluent includes aqueous or non-aqueous diluents or combination thereof.

Gel Composition

Nasal composition of the present invention can be formulated as gel composition of tapentadol for nasal administration to increase the residence time of the drug in the nasal mucosa so as to bring about complete absorption of drug.

A nasal carrier used in the gel composition is selected from mucoadhesive agent, viscosity modifying agent, flavoring agent, permeation enhancer, sweetener, taste-masking agent, solubilizer, humectant, chelating agent, buffering agent, solvents, co-solvents, surfactant, preservative, stabilizer and polymer. The pH of the nasal gel composition is within a range of 3.0 to 9.0, preferably from 3.0 to 8.0, more preferably from 3.0 to 7.0 and most preferably from 4.0-6.0.

In-Situ Gel Composition

Nasal formulation of the present invention can be formulated as liquid composition which forms a gel after nasal administration, can be hydrogel or organogel, preferably hydrogel which increase the residence time of drug to provide better absorption of the drug over a prolong period of time, thus may reduce dosing frequency. Theses composition will be in the form of solution under ambient conditions, which will form gel upon contact with the nasal mucosa. The composition consists of tapentadol or its pharmaceutically acceptable salt(s) solubilised in aqueous/non aqueous medium containing mucoadhesive agent(s). Composition may contain humectants to have a soothing effect on mucosa.

The pH of the nasal in-situ gel composition is in the range of 3.0 to 9.0, preferably from 3.0 to 8.0, more preferably from 3.0 to 7.0 and most preferably from 4.0-6.0. The preferred composition is nasally applied as a cytoadhesive or mucoadhesive composition which will have either thermo-responsive, ionotropic gelation, water triggered gelation/lyotropic systems or pH responsive bioadhesive properties or any combination of these.

A nasal carrier used in the in-situ gel composition is selected from in-situ gelling agent, mucoadhesive agent, humectants, thickening agents, permeation enhancer, chelating agent, flavoring agent, viscosity modifying agent, sweetener, taste masking agent, solubilizer, preservative, chelating agent, stabilizer, surfactant, solvents, co-solvents and buffering agent.

Powder Composition

Nasal composition of the present invention can be formulated as a powder composition having improved drug absorbability via nasal mucosa. More specifically, the present invention relates to powder composition for nasal administration that exhibit high maximum blood concentration by using tapentadol having a specific particle size. The composition may contains only tapentadol or along with nasal carrier.

Nasal carrier used in the powder composition is selected from mucoadhesive agent, lubricants, permeation enhancer, flavoring agent, sweetener, taste-masking agent, diluents or bulking agents and/or preservative.

According to present invention, average particle size of the formulated drug in powdered form is less than 300 micron, preferably less than 200 micron, most preferably in the range of 0.5 to 150 microns.

Micro/Nanoemulsion Composition

Nasal composition of the present invention can be formulated as micro/nanoemulsion composition of tapentadol for nasal administration having improved drug absorbability via nasal mucosa. The emulsion comprises of an aqueous phase, an oily phase and surfactant to stabilize the emulsion. The oily phase comprises of fatty acid esters and surfactant is primarily hydrophilic.

The micro/nanoemulsion composition is not limited to any particular pH. However, generally for nasal administration a mildly acid pH will be preferred. The pH ranges from about 3.0 to 9.0 are preferred. More preferably pH ranges from 3.0 to 8.0, most preferably from 3.0 to 7.0 and most preferably from 4.0-6.0.

Nasal carrier used in the micro/nanoemulsion composition is selected from solvents, surfactant, mucoadhesive agent, isotonicity agent, permeation enhancer, chelating agent, flavoring agent, viscosity modifying agent, taste masking agent, solubilizer, buffering agent, sweetener and oil.

Liposome Composition

Nasal composition of the present invention can be formulated as liposomal composition of tapentadol for nasal administration includes phospholipids, the composition may contain other excipients to enhance the shelf life of liposomal composition.

The liposome composition is not limited to any particular pH. However, generally for nasal administration a mildly acid pH will be preferred. The pH ranges from about 3.0 to 9.0 are preferred. More preferably pH ranges from 3.0 to 8.0, most preferably from 3.0 to 7.0 and most preferably from 4.0-6.0.

Nasal carrier used in the liposome composition is selected from antioxidants, buffering agent, chelating agents, preservative, viscosity modifying agent, isotonicity agent, flavoring agent, sweetener and phospholipids.

In some embodiments of the present invention, the composition contains a diluent(s). Examples of aqueous diluent include, but are not limited to, saline, water, dextrose or combinations thereof. Non-aqueous diluents include, but are not limited to, alcohols, particularly polyhydroxy alcohols such as propylene glycol, polyethylene glycol, glycerol, and vegetable and mineral oils. These aqueous and/or non-aqueous diluents can be added in various concentrations and combinations to form solutions, suspensions, oil in water emulsions or water in oil emulsions.

In some embodiments of the present invention, the composition comprises solvent(s) which can be aqueous or non-aqueous, polar or non-polar. Examples of solvent include, but are not limited to purified water, water for injection, aliphatic alcohols, polyhydric alcohols, butanol, glycols, such as propylene glycol, or medium chain alcohols, amines, or acids, saline solution, polyglycols, disodium lauryl B-iminodipropionate, (Monateric™ 1188M), alkyl polyglucosides (Atlox AL-2575), deceth-4 phosphate (Monafax™ 1214), Non-volatile benzoate ester (Prifer™ 6813), glycerine and the like or mixtures thereof.

In some embodiments of the present invention, the composition contains a preservative that is chosen in quantities that preserve the composition, but do not cause irritation of the nasal mucosa. Suitable preservative for use in some embodiments of the present invention include, but are not limited to, benzalkonium chloride, sodium benzoate, methyl, ethyl, propyl or butyl paraben, benzyl alcohol, phenylethyl alcohol, benzethonium chloride, chlorobutanol, potassium sorbate or combination thereof. A preferred preservative is benzalkonium chloride.

In some embodiments of the present invention, the composition is preservative-free. As used herein, preservative-free includes composition that does not contain any preservative.

In some embodiments of the present invention, the composition contains a buffering agent, it is chosen in quantities that preferably do not irritate the nasal mucosa. Buffering agent includes agent that adjusts pH changes. Preferred buffering agents for use in the present invention include, but are not limited to, salts of citrate, acetate, or phosphate. More preferred buffering agents are selected from sodium citrate, sodium acetate, sodium phosphate, and/or combinations thereof.

In some embodiments of the present invention, the composition contains an in-situ gelling agent(s). Examples of in-situ gelling agent(s) include, but are not limited to polyoxyethylene-polyoxypropylene copolymer (Poloxamer, Pluronic), PEO-PLLA diblock copolymer, PEG-PLGA-PEG triblock copolymer, Membrane Matrix (Matrigel), cellulose acetophalate latex, pectins, sodium alginate, polyacrylic polymers like carbopols, gellan gum and the like, either alone or in any combination thereof.

In some embodiments of the present invention, the composition contains a thickening agent(s). Examples of thickening agent include, but are not limited to CMC, HPMC, sodium alginate, collagen, gelatin, and hyaluronic acid, polyacrylic polymers like Carbopol, gellan gum (Gelrite), and xyloglucan alone or in combination.

In some embodiments of the present invention, the composition contains oil. Examples of oil include, but are not limited to cod liver oil, lanolin oil, mink oil, orange roughy oil, and shark liver oil, almond oil, apricot kernel oil, avocado oil, castor oil, coconut oil, corn oil, evening primrose oil, jojoba oil, olive oil, safflower oil, sesame oil, soybean oil, and wheat germ oil, oleoyl macrogol-6 glycerides (Labrafil® M 1944 CS), linoleoyl macrogol-6 glycerides (Labrafil® M 2125 CS), lauroyl macrogol-6 glycerides (Labrafil® M 2130 CS), propylene glycol dicaprylocaprate (Labrafac™), medium-chain triglycerides (Lipophile WL 1349), propylene glycol dicaprylocaprate (Labrafac™ PG), polyoxyethylene (6) caprylic/capric glycerides (Acconon CC-6), polyglycerol esters of oleic acid (Caprol MPGO), glyceryl monocaprylate (Capmul MCM) and some silicone oils, alone or in combination.

In some embodiments of the present invention, the composition contains a surfactant. Examples of surfactant include, but are not limited to polyoxyethylen-sorbitan fatty acid esters (Tween), polyethylene-polypropylene glycols, polyoxyethylene-stearates, polyoxyethylene alkyl ethers, e.g. polyoxyethylene monolauryl ether, alkylphenylpolyoxy-ethylene ethers (Triton-X), polyoxyethylene-polyoxypropylene copolymer (Poloxamer, Pluronic), and sodium dodecyl sulphate (SDS), alone or in combination. When one or more surfactants is employed, the amount surfactant present in the compositions of the invention will vary depending on the particular surfactant chosen, the particular mode of administration (e.g. drop or spray) and the effect desired.

In some embodiments of the present invention, the composition contains a co-solvent(s). Example of co-solvent includes, but is not limited to benzyl alcohol, butanol, glycols, $C_3$-$C_9$ chain alcohols, amines, acids, saline solution and polyglycols.

In some embodiments of the present invention, the composition contains a mucoadhesive agent(s). Examples of mucoadhesive agent include, but are not limited to such as polyacrylic polymers like carbopols, polycarbophil, carboxymethylcellulose, MCC, hydroxyethylcellulose, hydroxypropyl cellulose, hydroxypropylmethyl cellulose, methylcellulose, poloxamers, pectin, xanthan gums, alginates, gelatin alone or in any combination thereof.

In some embodiments of the present invention, the composition contains isotonicity agent(s). Examples of isotonicity agent include, but are not limited to sodium chloride (NaCl), potassium chloride, sugars and sugar alcohols like glucose, dextrose, sucrose, mannitol, glycerol and any component from the group of amino acids, alone or in any combination thereof.

In some embodiments of the present invention, the composition contains a permeation enhancer(s). Examples of permeation enhancer include, but are not limited to fatty acid, medium chain glyceride, surfactant, steroidal detergent, acyl carnitine, alkanoyl choline, d-alpha tocopheryl polyethylene glycol 1000 succinate (Vitamin E TPGS), macrogol (15)-hydroxystearate (Solutol HS 15), N-acetylated amino acid, esters, salts and derivatives thereof alone or in any combination thereof.

In some embodiments of the present invention, the composition contains a viscosity modifying agent(s). Examples of viscosity modifying agent include, but are not limited to methyl cellulose, carboxymethylcellulose sodium, ethyl cellulose, carrageenen, polyacrylic polymers like carbopol, polyethyleneglycol, or cross linked polyvinylpyrrolidone, hydroxypropylmethyl cellulose, sodium alginate, collagen, gelatin, and hyaluronic acid, alone or in any combination thereof.

In some embodiments of the present invention, the composition contains a polymer(s). Examples of polymers include, but are not limited to hydroxypropyl cellulose, hydroxypropyl methyl cellulose, methyl cellulose, and carboxymethyl cellulose sodium crystalline cellulose, α-cellulose, PVP, cross-linked carboxymethyl cellulose sodium, cross-linked starch, gelatin, casein, gum tragacanth, xanthan gum, chitin, carbopol, poloxamer (Pluronics), PEO-PLLA diblock copolymer, PEG-PLGA-PEG triblock copolymer, membrane matrix (Matrigel), cellulose acetophalate latex, pectins, sodium alginate, gellan gum alone or in any combination thereof.

In some embodiments of the present invention, the composition contains a stabilizer(s). Examples of stabilizers include, but are not limited to amino acids such as lysine phenylalanine, leucine and the like, sugars including raffinose, inulin and the like, alpha-tocopherol, ascorbic acid, butylated hydroxyanisole, butylated hydroxytoluene, citric acid, fumaric acid, malic acid, monothioglycerol, propionic acid, propyl gallate, sodium ascorbate, sodium bisulfite, sodium metabisulfite, potassium metabisulfite, sodium sulfite, tartaric acid and vitamin E.

In some embodiments of the present invention, the composition contains a chelating agent(s). Examples of chelating agent include, but are not limited to EDTA, polycarboxylic acids and salts thereof such as tartaric acid, citric acid, gluconic acid, malic acid and the like; polyphosphates and salts thereof, such as polyphosphates with n=2 or more; copolymers of carboxylic polymers such as PVM/MA copolymer (Gantrez); copolymers of phosphate polymers and salts thereof, alone or in any combination thereof.

In some embodiments of the present invention, the composition contains a humectant(s), preferably aqueous humectant(s). Examples of aqueous humectants include, but are not limited to PEG, glycerol, sorbitol, sucrose, mannitol, xylitol, maltitol, polymeric polyols like polydextrose, or natural extracts like quillaia, lactic acid or urea, alone or in any combination thereof.

In some embodiments of the present invention, the composition contains a sweetener. The sweetener is selected from the group comprising of aspartame, saccharin sodium, acesulfame potassium, dried invert sugar, dextrose, glucose, fructose, galactose, levulose, maltose, neotame, sucralose, neotame and mixture thereof. Preferred sweetener is sucralose. Another preferred sweetener is neotame.

In some embodiments of the present invention, the composition contains an antioxidant. Examples of antioxidant(s) include, but are not limited to alpha-tocopherol, ascorbic acid, butylated hydroxyanisole, butylated hydroxytoluene, citric acid, fumaric acid, malic acid, monothioglycerol, propionic acid, propyl gallate, sodium ascorbate, sodium bisulfite, sodium metabisulfite, potassium metabisulfite, sodium sulfite, tartaric acid or vitamin E, alone or in any combination thereof.

In some embodiments of the present invention, the composition contains a taste-masking agent. Examples of taste-masking agent(s) include, but are not limited to sucralose, dimethylaminoethyl methacrylate polymer, hydroxypropylmethylcellulose, hydroxypropyl cellulose, gelatin, sodium carboxymethylcellulose, aspartame, saccharin sodium, acesulfame potassium, neotame, methylcellulose, polyethylene glycol alone or in any combination thereof.

In some embodiments of the present invention, the nasal composition contains a lubricant. Examples of lubricant(s) include, but are not limited to aluminium stearate, sodium stearate, sodium stearyl fumarate, polyethylene glycol alone or in any combination thereof.

In some embodiments of the present invention, the nasal composition contains a bulking agent. Examples of bulking agent(s) include, but are not limited to mannitol, sorbitol, lactose, maltose, dextrose, sucrose, maltodextrin, corn starch, hyroxypropylmethylcellulose, hydroxypropyl cellulose, microcrystalline cellulose, hydroxyethyl cellulose, hydroxymethylcellulose, sodium carboxymethylcellulose alone or in any combination thereof.

In some embodiments of the present invention, the composition contains a colorant. Examples of colorant(s) include, but are not limited to Red no. 2, D&C BLUE NO. 1, 2, 6, D&C YELLOW NO. 10, 5, 6, D&C YELLOW NO. 6 LAKE, FD&C yellow NO. 5 alone or in any combination thereof.

In some embodiments of the present invention, the composition contains a phospholipid. Examples of phospholipid(s) include, but are not limited to phosphatidylcholine (PC), phosphatidylglycerol (PG), phosphatidylinositol (PI), phosphatidic acid (PA), phosphatidylserine (PS), or mixtures, Stearylamine (SA), Cholesterol, dilaurylphosphatidylcholine (DLPC), dimyristolphosphatidylcholine (DMPC), dipalmitoylphosphatidylcholine (DPPC), dilaurylphosphatidylglycerol (DLPG), dimyristolphosphatidylglycerol (DMPG), dioleoylphosphatidylcholine (DOPC), dioleoylphosphatidylglycerol (DOPG), dioleoylphosphatidylethanolamine (DOPE), cholesteryl sulphate and the like, alone or in any combination thereof.

In some embodiments of the present invention, the composition contains a flavoring agent. Examples of flavoring agent(s) include, but are not limited to flavor anise, flavor apple, flavor apricot, flavor Banana, flavor bitter mask, flavor buttermint, flavor citrus, flavor orange, flavor menthol mint, flavor mint, flavor peppermint alone or in any combination thereof.

In some embodiments of the present invention, the composition contains solubilizer. Examples of solubilizer include, but are not limited to d-alpha tocopheryl polyethylene glycol 1000 succinate (Vitamin E TPGS), macrogol (15)-hydroxystearate (Solutol HS 15), polyoxyethylene-polyoxypropylene copolymer (Poloxamer, Pluronic), PEO-PLLA diblock copolymer, PEG-PLGA-PEG triblock, copolymer, cyclodextrins, hydroxypropyl betadex, polyoxyethylene castor oil derivatives, povidone, sulfobutylether-b-cyclodextrin, tricaprylin, triolein, glyceryl monostearate, sorbitan esters (sorbitan fatty acid esters), polyoxyethylene fatty acid esters alone or in combination thereof.

In some embodiments of the present invention, the composition contains crystal growth inhibitor. Examples of crystal growth inhibitor include, but are not limited to polysorbate 80, polysorbate 20 or macrogol-15-hydroxysterate, most preferably polyoxyethylene-polyoxypropylene copolymer or in combination thereof.

The pharmaceutical composition of the present invention can be administered through a nasal spray or any suitable nasal applicator. Nasal composition can be of multi dose container or unit dose container, preferably in multi dose container.

This specification also makes use of the following abbreviations:

CMC carboxymethylcellulose

HPMC hydroxypropylmethyl cellulose

MCC microcrystalline cellulose

PVP polyvinylpyrrolidone

PEO poly(ethylene oxide)

PLLA poly-l-lactide

PEG polyethylene glycol

PLGA poly(lactic-co-glycolic acid)

EDTA ethylenediaminetetraacetic acid

The invention will be further illustrated by the following examples, however, without restricting its scope to these embodiments.

EXAMPLE 1

| S. No. | Ingredients | Concentration Range (w/w) |
| --- | --- | --- |
| 1 | Tapentadol Hydrochloride | 5-50% |
| 2 | Sodium chloride | 0.5-2% |
| 3 | Benzalkonium chloride | 0.01-1% |
| 4 | Purified water | q.s. |

Procedure:
1. Sodium chloride is dissolved in purified water.
2. Weighed quantity of tapentadol hydrochloride is added to the solution obtained in step 1, followed by addition of benzalkonium chloride.
3. Make up the volume with purified water.

EXAMPLE 2

| S. No | Ingredients | Concentration Range(W/W) |
| --- | --- | --- |
| 1 | Tapentadol Hydrochloride | 5-50% |
| 2 | Sodium Chloride | 0.5-2% |
| 3 | Benzalkonium | 0.01-1% |
| 4 | Sucralose | 0.1-5% |
| 5 | Purified Water | q.s |

Procedure:
1. Sodium chloride and sucralose is dissolved in purified water.
2. Weighed quantity of tapentadol hydrochloride is dissolved in the solution obtained in step 1, followed by benzalkonium chloride.
3. Make up the volume with purified water.

EXAMPLE 3

| S. No | Ingredients | Concentration Range(w/w) |
| --- | --- | --- |
| 1 | Tapentadol Hydrochloride | 5-50% |
| 2 | Genu Pectin | 0.2-2% |
| 3 | Sodium alginate | 0.2-2% |
| 4 | Sorbitol | 0.2-5% |
| 5 | Benzalkonium Chloride | 0.01-1% |
| 6 | Purified Water | q.s |

Procedure:
1. Pectin and sodium alginate are dissolved in appropriate ratio in purified water.
2. Sodium chloride, sorbitol and benzalkonium chloride are dissolved separately in purified water then weighed quantity of tapentadol hydrochloride is added and dissolved.
3. Drug solution is then added in pectin alginate solution
4. Make up the volume with purified water.

EXAMPLE 4

| S. No | Ingredients | Concentration Range(w/w) |
| --- | --- | --- |
| 1 | Tapentadol | 5-50% |
| 2 | Polyethylene glycol 400 (PEG) | 5-25% |
| 3 | Propylene glycol | 50-95% |
| 4 | Butylate hydroxyl toluene | 0.01-2% |
| 5 | Sucralose | 0.1-5% |
| 6 | Benzalkonium chloride | 0.01-1% |

Procedure:
1. Weighed quantity of tapentadol is dissolved in PEG 400 and the solution is diluted with propylene glycol
2. Sucralose, Benzalkonium chloride and butylate hydroxy toluene are then added with stirring to composition of step 1.
3. Make up the volume with propylene glycol.

EXAMPLE 5

| Sr No | Ingredients | Concentration range (w/w) |
| --- | --- | --- |
| 1 | Tapentadol Hydrochloride | 5-50% |
| 2 | Sorbitol | 1-10% |
| 3 | Hydroxypropyl methyl cellulose | 0.05-5% |

| Sr No | Ingredients | Concentration range (w/w) |
|---|---|---|
| 4 | Sucralose | 0.1-5% |
| 5 | Benzalkonium chloride | 0.01-1% |
| 6 | Purified water | q.s |

Procedure:
1. Dissolve sorbitol in purified water.
2. Dissolve hydroxypropyl methyl cellulose in solution of step 1.
3. Dissolve sucralose followed by tapentadol hydrochloride to solution of step 2.
4. Add Benzalkonium chloride to solution of step 3.
5. Make up the volume with purified water.

EXAMPLE 6

| Sr No | Ingredients | Concentration range (w/v) |
|---|---|---|
| 1 | Tapentadol Hydrochloride | 25% |
| 2 | Hydroxypropylmethylcellulose (HPMC) (6 cps) | 0.1% |
| 3 | Neotame | 0.5% |
| 4 | Benzalkonium chloride (50%) | 0.02% |
| 5 | Spearmint supreme | 0.1% |
| 6 | Purified water | q.s |

Procedure:
1. Hydroxypropylmethylcellulose was dissolved in purified water to prepare a solution.
2. Neotame was added in the solution of step 1.
3. Tapentadol Hydrochloride was dissolved in solution of step 2.
4. Benzalkonium chloride was added to the solution of step 3 followed by addition of spearmint supreme.
6. Volume was made up with purified water.
pH=5.23

EXAMPLE 7

| Sr No | Ingredients | Ingredients |
|---|---|---|
| 1 | Tapentadol Hydrochloride | 25% |
| 2 | Sodium carboxymethylcellulose (MF) | 0.05% |
| 3 | Neotame | 0.5% |
| 4 | Benzalkonium chloride (50%) | 0.02% |
| 5 | Spearmint supreme | 0.1% |
| 6 | Purified water | q.s |

Procedure:
Procedure of Example 6 was followed replacing hydroxypropylmethylcellulose with Sodium Carboxymethylcellulose to prepare solution.
pH—5.15

EXAMPLE 8

| Sr No | Ingredients | Concentration range (w/v) |
|---|---|---|
| 1 | Tapentadol Hydrochloride | 25% w/v |
| 2 | Sodium carboxymethylcellulose (MF) | 0.15% w/v |
| 3 | Neotame | 0.5% w/v |
| 4 | Benzalkonium chloride (50%) | 0.02% w/v |
| 5 | Spearmint supreme | 0.1% w/v |
| 6 | Purified water | q.s |

Procedure:
Procedure of Example 6 was followed replacing hydroxypropylmethylcellulose with Sodium Carboxymethylcellulose to prepare solution.
pH=5.34

EXAMPLE 9

| Sr No | Ingredient | Concentration range (w/v) |
|---|---|---|
| 1 | Tapentadol Hydrochloride | 38.5% |
| 2 | Hydroxypropylmethylcellulose (HPMC) (6 cps) | 0.1% |
| 3 | Poloxamer 188 | 0.6% |
| 4 | Neotame | 0.5% |
| 5 | Benzalkonium chloride (50%) | 0.02% |
| 6 | Spearmint supreme | 0.1% |
| 7 | Water for Injection | q.s. |

Procedure:
Hydroxypropylmethylcellulose was dissolved purified water. Poloxamer 188 was added into the obtained solution and stirred to form homogenous solution. In the obtained solution, neotame was added. Tapentadol hydrochloride was dissolved in obtained solution, followed by addition of benzalkonium chloride and spearmint supreme. Volume of the solution was made up with purified water.
pH=4.69

EXAMPLE 10

| Sr No | Ingredient | Concentration range (w/v) |
|---|---|---|
| 1 | Tapentadol Hydrochloride | 25% |
| 2 | Hydroxypropylmethylcellulos (HPMC) (6 cps) | 0.1% |
| 3 | Poloxamer 188 | 0.6% |
| 4 | Neotame | 0.5% |
| 5 | Benzalkonium chloride (50%) | 0.02% |
| 6 | Spearmint supreme | 0.1% |
| 7 | Water for Injection | q.s. |

Procedure:
Procedure of Example 9 was followed by using 25% of tapentadol concentration.
pH=4.72

EXAMPLE 11

In-vivo characterization:
Animals (NZW Rabbit) were kept on fasting overnight. Next day Tapentadol Hydrochloride (solution of tapentadol hydrochloride and 1% NaCl) was administered by oral route using an oral gavage and graduated syringe at the dose of 5 mg/kg (dosage volume of 2 ml/kg body weight and 2.5 mg/ml concentration). For intranasal study 25 µl of formulation obtained in example 6, 7 and 8 were instilled into each nostril using metered dose pump VP-7 at the dose of 5 mg/kg (each 25 µl delivers 6.25 mg Tapentadol Hydrochloride) administering 12.5 mg dose. Results are summarized in Table 1 and FIG. 1.

TABLE 1

| PK Parameters | Units | Oral (12.5 mg) | | Example 6 | | Example 7 | | Example 8 | |
|---|---|---|---|---|---|---|---|---|---|
| | | Mean | SD | Mean | SD | Mean | SD | Mean | SD |
| Tmax | hr | 1.63 | 1.60 | 0.13 | 0.00 | 0.13 | 0.00 | 0.16 | 0.06 |
| Cmax | ng/mL | 123.51 | 137.89 | 161.38 | 22.27 | 80.05 | 32.74 | 86.53 | 20.13 |
| AUClast | Hr * ng/mL | 160.73 | 133.16 | 164.44 | 35.08 | 95.36 | 38.37 | 98.75 | 40.32 |

EXAMPLE 12

Droplet size distribution:

Droplet size distribution was checked by spraying composition according to example 9 and 10 with two different nasal pumps (100 µl and 130 µl) at a distance of 3 cm and 6 cm by using Spraytec® system with innova systems automated velocity based actuator and computed with NSS Spray View® software system. Droplet size distribution was found out to ascertain the effective droplet size pattern. Results are summarized in Table 2.

TABLE 2

| Parameter | | Example 10 (100 µl) | | Example 9 (100 µl) | | Example 9 (130 µl) | |
|---|---|---|---|---|---|---|---|
| Distance | | 3 cm | 6 cm | 3 cm | 6 cm | 3 cm | 6 cm |
| Mean | Dv(10) (µm) | 15.3 | 19.1 | 18.3 | 23.3 | 18.18 | 25.12 |
| | Dv(50) (µm) | 36.7 | 41.2 | 44.9 | 54.0 | 55.06 | 58.437 |
| | Dv(90) (µm) | 98.0 | 108.6 | 153.5 | 161.5 | 163.53 | 168.47 |
| | D[4][3](µm) | 52.9 | 76.2 | 69.4 | 78.2 | 79.143 | 81.897 |
| | % V < 10µ (%) | 3.5 | 2.7 | 2.2 | 1.8 | 2.832 | 1.3307 |

The invention claimed is:

1. A method of treating pain comprising:
   administering to a human in need thereof, a unit dose of a nasal composition by intranasal route, wherein the nasal composition comprises:
   (a) 5-50% of an active pharmaceutical ingredient consisting of tapentadol hydrochloride and
   (b) a nasal carrier comprising 0.1% w/v of hydroxypropylmethylcellulose and 0.6% w/v of polyoxyethylene-polyoxypropylene copolymer,
   wherein the nasal composition is formulated as a liquid composition, the unit dose of the nasal composition has a volume of 100 µl and the nasal composition has droplet size distribution Dv(90) less than 200 µm and a viscosity equal to or less than 100 cps.

2. The method according to claim 1, wherein the nasal composition has a pH in the range of 3.0 to 9.0.

3. The method according to claim 1, wherein the liquid composition is in the form of aqueous solution.

4. The method according to claim 1, wherein the composition further comprises an agent selected from the group consisting of buffering agent, isotonicity agent, preservative, permeation enhancer, stabilizer, solubilizer chelating agent, antioxidant, mucoadhesive agent, viscosity modifying agent, humectants, sweetener, taste masking agent, solvents, co-solvents, in-situ gelling agent, surfactant, polymer, thickening agent, lubricant, bulking agent, colorant, oil, phospholipids and flavoring agent.

5. The method according to claim 1 wherein the unit dose of the nasal composition has a droplet size distribution Dv(90) less than 180 µm.

6. A method of treating pain comprising:
   administering to a human in need thereof, a unit dose of a liquid nasal composition by intranasal route, wherein the nasal composition comprises:
   (a) 5-50% of an active pharmaceutical ingredient consisting of tapentadol hydrochloride and
   (b) a nasal carrier comprising 0.1% w/v of hydroxypropylmethylcellulose and 0.6% w/v of polyoxyethylene-polyoxypropylene copolymer,
   wherein the unit dose of the nasal composition has a volume of 100 µl and the nasal composition has droplet size distribution Dv(90) less than 200 µm and a viscosity equal to or less than 100 cps, and
   wherein the unit dose of the nasal composition achieves a Cmax in less than 45 minutes and wherein inter-subject variability in AUC when administering the unit dose of 100 µl volume is less than 50%.

7. The method according to claim 1, wherein administering the unit dose of the nasal composition provides lower inter-subject variability compared to an oral formulation containing the same amount of tapentadol.

8. The method according to claim 6, wherein administering the unit dose of the nasal composition provides lower inter-subject variability compared to an oral formulation containing the same amount of tapentadol.

* * * * *